(12) United States Patent
Biedermann et al.

(10) Patent No.: US 8,353,936 B2
(45) Date of Patent: Jan. 15, 2013

(54) ROD CONNECTION IN A SURGICAL DEVICE AND ROD-SHAPED BONE STABILIZATION DEVICE COMPRISING THE SAME

(75) Inventors: Lutz Biedermann, VS-Villingen (DE); Wilfried Matthis, Weisweil (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 844 days.

(21) Appl. No.: 12/242,649

(22) Filed: Sep. 30, 2008

(65) Prior Publication Data
US 2009/0099599 A1    Apr. 16, 2009

Related U.S. Application Data

(60) Provisional application No. 60/979,201, filed on Oct. 11, 2007.

(30) Foreign Application Priority Data

Oct. 11, 2007    (EP) .................................. 07019941

(51) Int. Cl.
*A61B 17/70*    (2006.01)
(52) U.S. Cl. ........ 606/259; 606/254; 606/257; 606/264; 606/279
(58) Field of Classification Search ........... 606/254–275
See application file for complete search history.

(56) References Cited

U.S. PATENT DOCUMENTS

| 5,645,386 | A | 7/1997 | Damm et al. | |
|---|---|---|---|---|
| 7,153,075 | B2 | 12/2006 | Sommer et al. | |
| 7,811,309 | B2 * | 10/2010 | Timm et al. | 606/257 |
| 8,002,803 | B2 * | 8/2011 | Winslow et al. | 606/257 |
| 2004/0115026 | A1 | 6/2004 | Sommer et al. | |
| 2004/0236327 | A1 | 11/2004 | Paul et al. | |
| 2005/0085815 | A1 | 4/2005 | Harms et al. | |
| 2005/0131407 | A1 * | 6/2005 | Sicvol et al. | 606/61 |
| 2005/0203517 | A1 * | 9/2005 | Jahng et al. | 606/61 |
| 2007/0055244 | A1 * | 3/2007 | Jackson | 606/61 |

FOREIGN PATENT DOCUMENTS

| DE | 43 18 494 C1 | 2/1995 |
|---|---|---|
| DE | 102 58 149 A1 | 7/2004 |
| JP | 2007-502692 A | 2/2007 |
| JP | 2008-080375 | 4/2008 |
| WO | WO 2004/105577 A2 | 12/2004 |
| WO | WO 2005/094704 A1 | 10/2005 |

* cited by examiner

OTHER PUBLICATIONS

Search Report for European Patent Application No. EP 07 019 941.9, filed Oct. 11, 2007, Applicant Biedermann Motech GmbH, European Search Report datedMar. 26, 2008 and mailed Apr. 8, 2008 (6 pgs.).
Japanese office action dated Apr. 17, 2012 for Application No. 2008-260605, 4 pages and English translation, 5 pages (parallel application).

*Primary Examiner* — Ellen C Hammond
(74) *Attorney, Agent, or Firm* — Christie, Parker & Hale, LLP

(57) ABSTRACT

A rod connection for fixing a rod part in a surgical device within a bore of a rod receiving member includes the rod receiving member having a bore having an inner diameter, the rod part having an outer diameter, the rod part being introduced into the bore, wherein the inner diameter of the bore and the outer diameter of the rod part are selected, such that the rod part is press-fitted into the bore of the rod receiving member. The bore has an inner wall surface opposing an outer wall surface of the rod part, the inner wall surface or the outer wall surface being provided with at least one recess in order to reduce a contact surface area between the rod part and the rod receiving member.

20 Claims, 8 Drawing Sheets

Fig 1 (PRIOR ART)
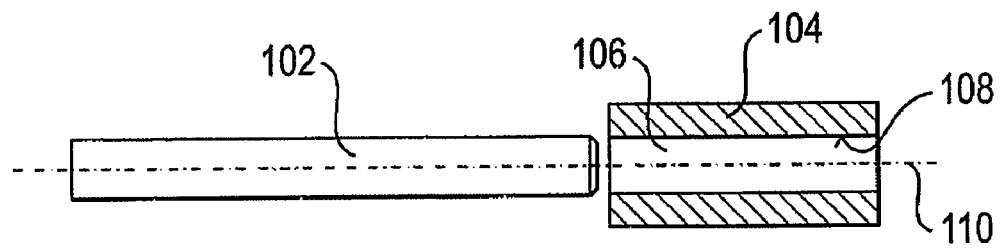
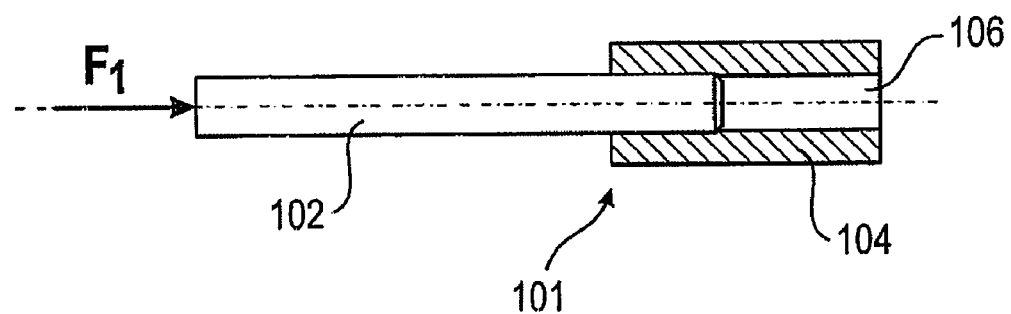
Fig. 2
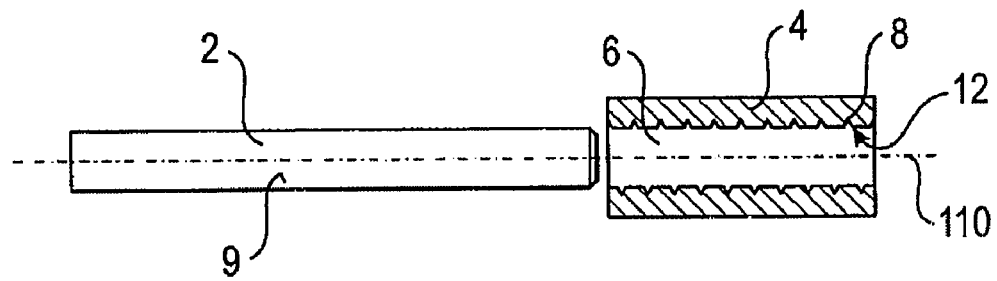
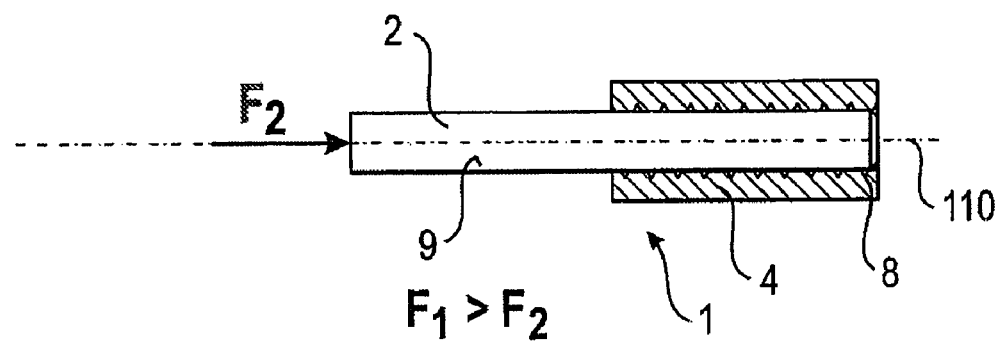
$F_1 > F_2$ Stress = Smax 433,91 Max
364,67
295,43
226,19
156,95
87,711
18,471
-50,769
-120,01
-189,25 Min Stress = Smax 323,3 Max
205,15
86,997
-31,157
-149,31
-267,47
-385,62
-503,77
-621,93
-740,08 Min

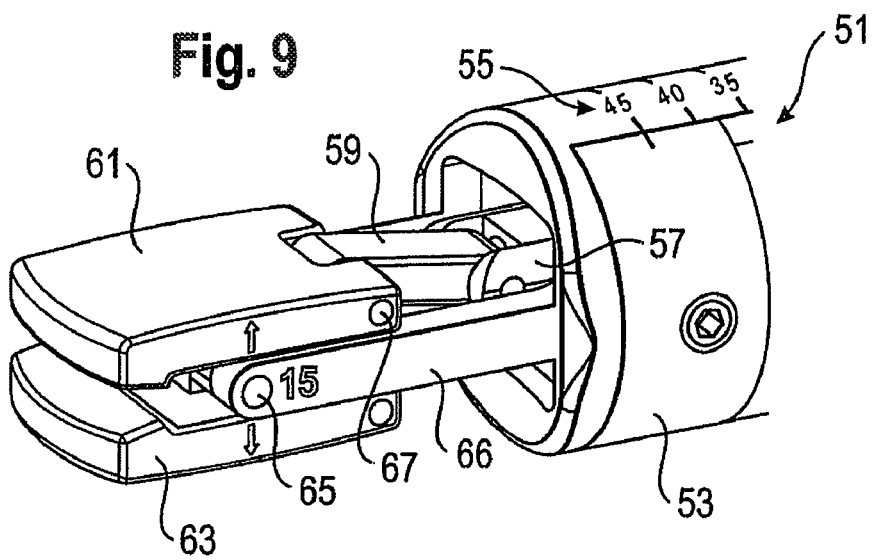
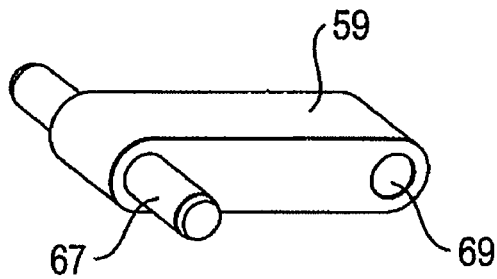
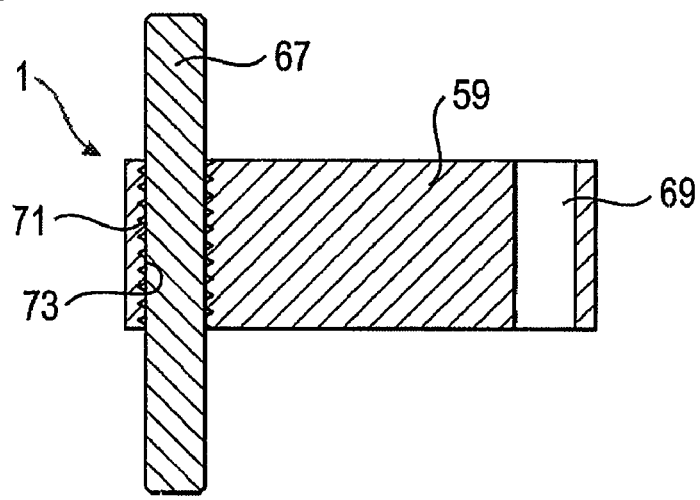
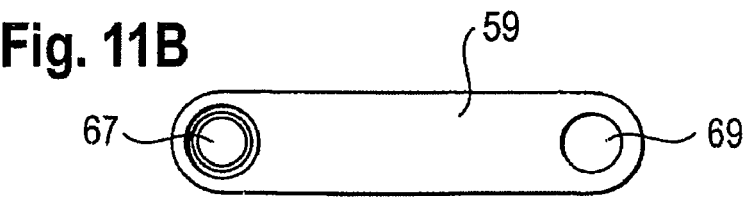

ROD CONNECTION IN A SURGICAL DEVICE AND ROD-SHAPED BONE STABILIZATION DEVICE COMPRISING THE SAME

CROSS-REFERENCE TO RELATED APPLICATION(S)

The present application claims the benefit of U.S. Provisional Patent Application Ser. No. 60/979,201, filed Oct. 11, 2007, the contents of which are hereby incorporated by reference in their entirety, and claims priority from European Patent Application, 07019941.9, filed Oct. 11, 2007, the contents of which are hereby incorporated by reference in their entirety.

BACKGROUND OF THE INVENTION

The invention relates to a rod connection provided in a surgical device.

Surgical devices may be composed of several components, which are adjoined with each other depending on the application either upon assembly of the respective device by the manufacturer or at the instance of surgery. Thus a connection between those components has to be provided, which for example secures a predetermined degree of reliability of the device in view of strain, bending and torsion stress, when this connection represents a rigid or fixed interface between the components.

In clinical surgery, the materials selected for the distinct components of the surgical device may be, among others, bio-compatible metals such as Titanium or Nitinol, a Nickel-Titanium alloy, or synthetic materials such as PEEK (polyetheretherketone) optionally being carbon fibre reinforced. The type of connection between the components commonly also depends on the materials involved.

For example in the case of two components made from metal, a connection may be established by providing a bore in one component (rod receiving member), into which is press-fitted a rod-like member of the other component, which has an interference with regard to the bore. In other words, in a disassembled state, the rod-like member (rod part) has an outer diameter larger than the inner diameter of the bore.

The corresponding amount of interference is chosen depending on the materials involved, and more specifically depending on the respective friction coefficients. The interference is further chosen such that in case of both a maximum value and a minimum value of a tolerance range with respect to the corresponding diameters a reliable connection is maintained.

In various applications in clinical surgery there is a continuing demand to provide components having a reduced size while maintaining its reliability with respect to external force transfer, which also act on the connections established in the devices.

With regard to the above mentioned press-fit connections, it may be observed that with decreasing diameters of the bore and the rod, a minimum bilateral tolerance of 5 µm increases its influence on the connection design. Consequently, with decreasing sizes of the diameters, the relative amount of interference increases.

As a result, there is a tendency to provide rod connections in clinical surgery, which may require considerable axial forces to assemble the components.

Based on the foregoing, there is a need to provide a reliable rod connection which allows a rod to be inserted into a bore with a moderate axial force.

SUMMARY OF THE INVENTION

A rod connection according to aspects of the disclosure includes a rod receiving member comprising a bore and a rod part introduced within the bore. An inner diameter of the bore and an outer diameter of the rod are selected, such that the rod part is press-fitted into the bore to yield a reliable press-fit or interference fit connection between the two parts.

According to one aspect, a rod receiving member has a bore and a rod part to be inserted into the bore achieves a press-fitted rod connection, wherein the bore has an inner surface and the rod part has an outer surface. A recess is formed in the inner wall surface or the outer wall surface, such that a contact surface area between the rod part and the bore of the rod receiving member is reduced.

Accordingly, a frictional force between both wall surfaces is also reduced. Insertion of the rod part into the bore upon assembly is thus facilitated. Meanwhile, the length of the bore necessary to stably support the rod part with regard to a bending momentum can be retained.

The recess provided in the inner wall surface may be formed as a homogeneously distributed pattern within the bore. In one specific embodiment, the recess is provided as an internal thread within the bore. However, it is noted that any type of recess or recesses suitable to efficiently reduce the contact surface area may be utilized with the present invention.

In an alternative embodiment, the recess may instead be provided in the outer wall surface of the rod part, e.g., as a homogeneously distributed pattern, more specifically as an external thread.

It is noted that the internal thread is not intended to engage with a corresponding external thread of the rod part, however, the invention shall not be limited accordingly. A thread may be easily manufactured in a controlled manner. A reduced amount of surface contact area may further be controlled without strong efforts.

The rod connection can be used in conjunction with metals commonly employed in clinical surgery. Those metals such as Titanium or Titanium alloy, particularly Nitinol, have a low thermal expansion coefficient while exhibiting galling between the components due to high pressure and relative movement.

The rod connection can be applied in bone stabilization devices for connecting two or more bone fixation elements, which reveal a dynamic behaviour due to the presence of a flexible section. The flexible section extends between a first and a second section, which provide a connection to the bone fixation elements, e.g., bone screws.

The rod receiving member of the rod connection according to this aspect of the invention is rigidly fixed to the first section, while the corresponding rod part extends through the flexible section towards the second section, where it is slidably supported with its free end. The rod part serves to stabilize the device against bending and efficiently transmits the bending moments applied from externally via its fixated end in the bore of the rod receiving member and via the guiding support at its free end. Thereby, the full length of the bore is retained to provide sufficient support while the recess serves to reduce the forces necessary to insert the rod part in bore.

BRIEF DESCRIPTION OF THE DRAWINGS

The invention will be better understood with reference to specific embodiments of the invention when taken in conjunction with the accompanying drawings. Therein, FIG. 1 shows in a schematical representation a rod connection of a surgery device according to prior art;

FIG. 2 shows a schematical representation of a rod connection similar to FIG. 1, but with regard to an aspect of the invention;

FIG. 9 shows a perspective view of an angle measurement device having a rod connection according to a second embodiment of the invention;

FIG. 10 shows a partial enlarged view of the rod connection of the second embodiment including a pushing rod as a rod receiving member and a rotational shaft as a rod part fixed therein;

FIG. 11A shows a cross-sectional view of the rod connection of FIG. 10;

FIG. 11B shows a side elevation view of the rod connection of FIG. 10;

DETAILED DESCRIPTION

Figure 3:
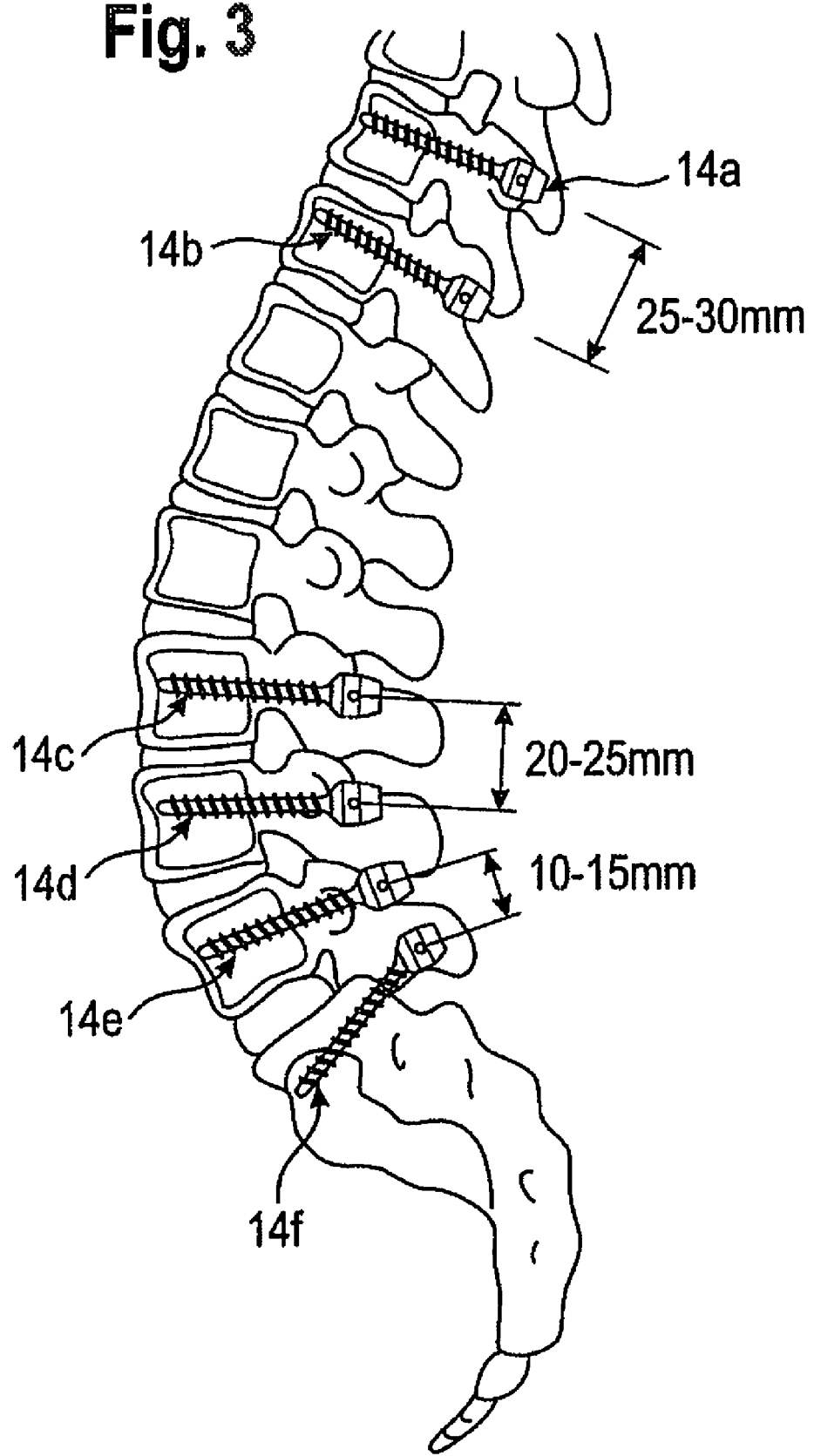
FIG. 3 shows an illustration of the spinal column.
Figure 4:
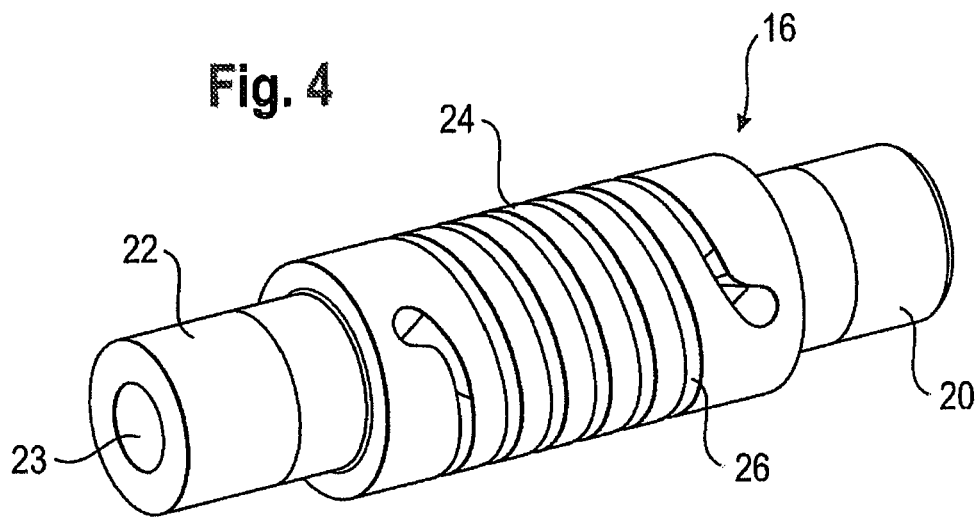
FIG. 4 shows in a perspective partial view a bone stabilization device including a rod connection according to a first embodiment.

A schematical representation of a rod connection 101 as typically used in a surgery device according to prior art is shown in FIG. 1. A rod-like member 102 is placed in front of a rod receiving member 104, which is provided with a bore 106 (see upper part of FIG. 1). The rod-like member 102 and the bore 106 are axially symmetric with respect to longitudinal axis 110.

The bore 106 further has an inner (cylindrical) wall surface 108, which is straight, i.e., the inner wall surface neither has projections nor is it provided with recesses at least within an area designed to receive the rod-like member 102. The rod-like member 102 has an outer diameter, which is slightly larger than an inner diameter of the bore 106 in order to provide an interference that results in a secure press-fitted connection between both members.

Hence, exertion of a predetermined force $F_1$ along the longitudinal axis 110 is needed to insert the rod-like member 102 into the bore 106 (bottom part of FIG. 1). Therein, the force $F_1$ is balanced by the frictional forces resulting from the high pressure.

A corresponding schematic representation of a rod connection 1 revealing some of the basic principles of the invention is shown in FIG. 2. A rod-like member 2, which may be similar to the rod-like member 102 of the device shown in FIG. 1, is to be inserted into a bore 6 of a rod receiving member 4 (upper part of FIG. 2). The materials selected for both members are the same as in the example of FIG. 1.

However, in contrast to FIG. 1 the bore 6 is provided with a recess or more specifically with a metric thread 12 formed on an inner wall surface 8 of the bore 6. The core diameter or inner diameter of the bore 6 may be similar to that detailed with regard to FIG. 1. Considering the same outer diameter of the rod-like member 2 as that of member 102, a predetermined insertion force $F_2$ is necessary to fit the rod-like member 2 in the bore 6.

The insertion force $F_2$ is smaller than the insertion force $F_1$ due to the presence of the metric thread formed in the inner wall surface 8 according to the rod connection 1 shown in FIG. 2. The metric thread 12 reduces the contact surface area between an outer wall surface 9 of the rod-like member 2 and the inner wall surface 8 of the rod receiving member 4. As a result, the frictional force acting against the insertion force $F_2$ is also reduced.

In the following, two more embodiments of surgery devices according to the invention will be explained in more detail. However, it will become apparent to a person of ordinary skill in the art, that the rod connection proposed herein may applied to various other surgery devices while yielding similar effects without departing from the scope as set forth, herein and in the appended claims.

A first embodiment concerning a bone stabilization device is detailed with regard to FIGS. 3-8. FIG. 3 shows a lower part of the spine anatomy in conjunction with variously positioned bone fixation elements 14a-14f. The bone fixation elements include a bone anchoring element such as a bone screw and a receiving part for receiving and fixing, e.g., a head portion of the bone screw. Each of the bone fixation elements 14a-14f is anchored in one vertebrae of either the thoracic or lumbar spine.

A bone stabilization device may include a rod device 16 (not shown in FIG. 3) which connects at least two of the bone fixation elements 14a-14f. As shown in the partial views of FIGS. 4, 5A and 5B, the rod includes a first section 20, a second section 22 and a flexible section 24 extending between the sections 20, 22. Note that the sections 20, 22 are cut at the left and right ends, respectively, for illustration purposes. The bone fixation elements 14a-14f are arranged according to anatomy and the minimum connection length of the rod device 16. The rod is inserted to the bone fixation elements and fixed by tightening the set screws onto the rigid first and second sections 20, 22.

The flexible element 24 and the two sections 20, 22 are preferably made of Titanium, a Titanium alloy or another bio-compatible metal material. The flexible element includes a cylindrical pipe in which a helical recess 26 is formed. Due to the recess 26 a longitudinal portion of the flexible element 24 is shaped like a coil spring. The flexible element 24 may function as a shock absorbing device in the axial direction.

As becomes apparent from FIG. 3, the mutual distances between two adjacent bone fixation elements 14a and 14b in the high thoracic part decreases from 25 mm-30 mm towards values of 10-15 mm for respective bone fixation elements 14e and 14f in the lower lumbar part (which stabilize L5-S1). Hence, the requirements regarding the downsizing of the rod device 16 and its components become stronger, when considering the lower lumbar part.

Figure 5A:
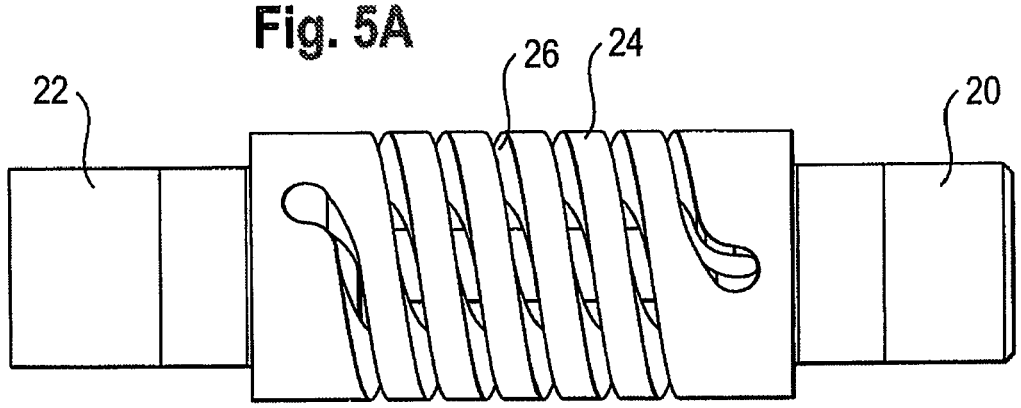
FIG. 5A shows a side view of the bone stabilization of FIG. 4.
Figure 5B:
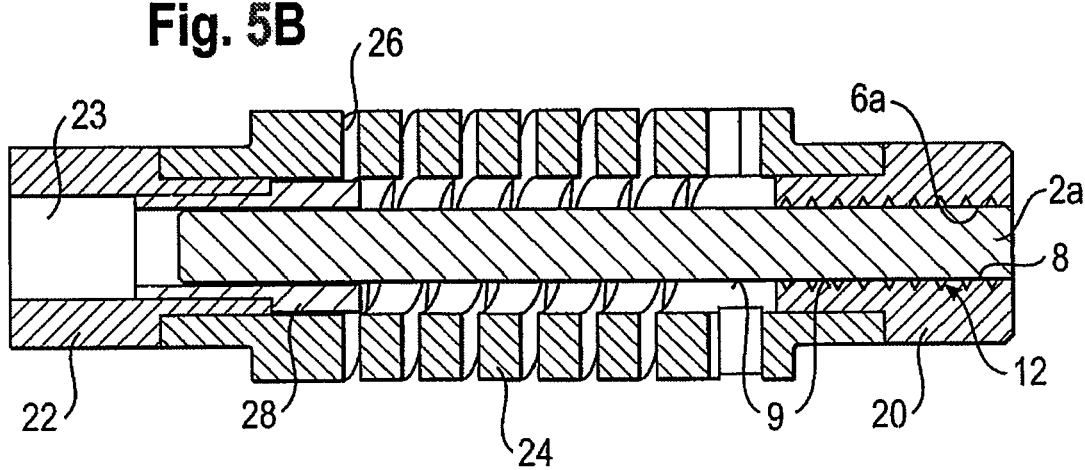
FIG. 5B shows a cross-sectional view of the bone stabilization of FIG. 4.

In the cross-sectional profile of the rod device 16 shown in FIG. 5B, a rod-like member 2a is displayed to extend from the first section 20 through the inner space of the spring-shaped flexible section 24 towards the second section 22. The member 2a may be represented by a Nitinol-wire. It serves to stabilize the rod device 16 against bending forces thereby allowing some degree of bending elasticity. Numeral 23 denotes a hollow space.

The right (fixed) end of the rod-like member 2a in FIG. 5B is press-fitted within bore 6a of the first section 20, the latter serving as the rod receiving member according to the invention—similar to member 4 in FIG. 2.

The left (free) end of the rod-like member 2a is slidably supported in guiding member 28, made from carbon reinforced PEEK for example. Accordingly, the rod-like member 2a may be freely moved in axial direction at its free end, when the flexible section 24 shortens or elongates due to external impacts.

Figure 6:
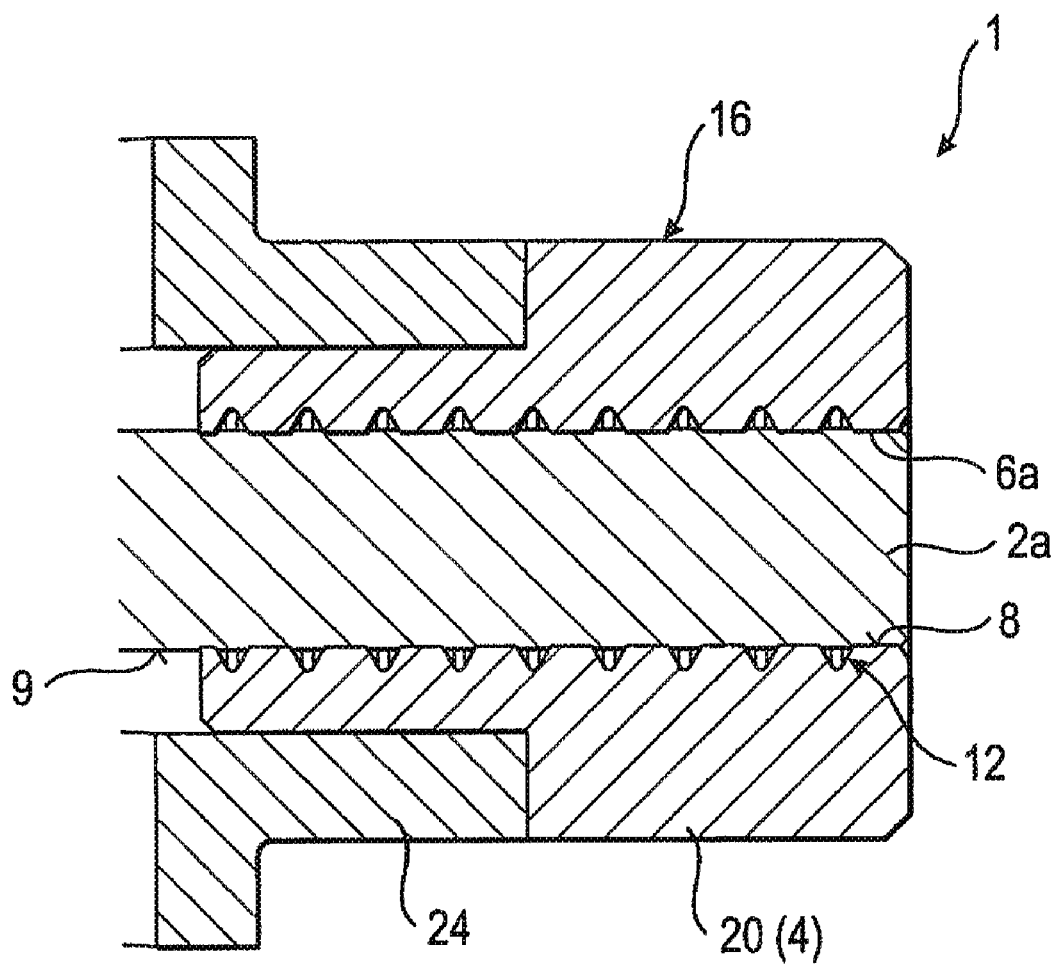
FIG. 6 shows an partial enlarged view of the first section of the device shown in FIG. 5B.

Returning to the fixed right end of the rod-like member 2a, the corresponding rod connection is established by press-fitting the end of member 2a within bore 6a formed in the first section 20. Thereby, a thread 12 which may optionally be metric is formed on an inner wall surface 8 of the bore. The rod-like member 2a on the contrary has an even outer wall surface 9, i.e., no thread is formed thereon. An enlarged partial view of the threaded bore 6a is shown in FIG. 6.

As stated above with reference to FIG. 2, the force necessary to insert the rod-like member is decreased while the stability and bending characteristics are maintained. This is particularly important in view of the reduced dimensions of the device: the above Nitinol-wire (member 2a) may have a diameter of 4 mm or less, more preferably 3 mm or less. According to one specific embodiment, the Nitinol-wire may even have a diameter of equal to or less than 2 mm.

In this case of small diameters, the common use of Titanium or Titanium alloys for both members 2a and 20 (or member 4 in FIG. 2) would conventionally put severe constraints on manufacturability of the connection. Titanium has a low thermal expansion coefficient of about $9 \cdot 10^{-6}$/K (compare, e.g., Aluminium with $24 \cdot 10^{-6}$/K). When the receiving member is then heated by, e.g., 200° C. in order expand its diameter of initially 2 mm, an increase of about 3.6 µm may be obtained. On the contrary, as stated above, tolerance ranges or widths of 5 µm may be obtained with improved manufacturing machines for the diameters of both the bores and rods, respectively. Thus, large insertion forces $F_1$ will be necessary to yield the connection, since the temperature difference cannot be further increased.

According to the embodiment, however, the thread 12 opposing the even surface of the rod-like member 2a helps in reducing the frictional force, which becomes apparent from the model simulation displayed in FIGS. 7A, 7B and 8A, 8B.

Figure 7A:
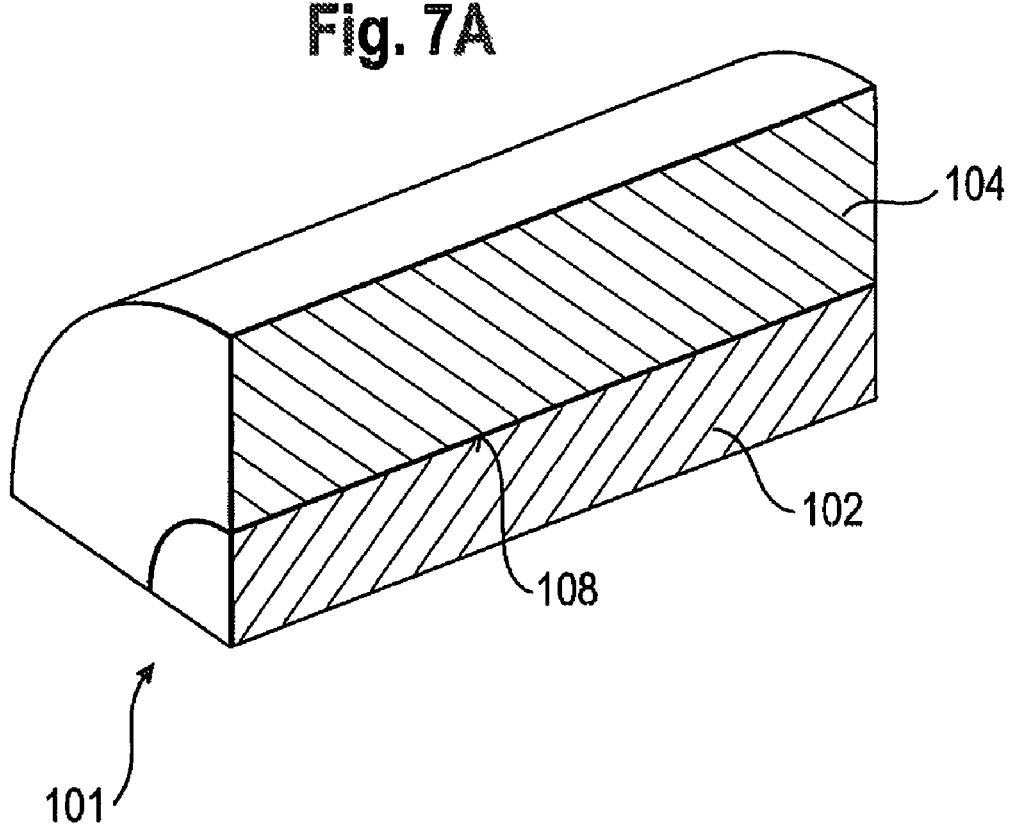
FIG. 7A shows an input model of a rod connection according to prior art for carrying out a simulation.
Figure 7B:
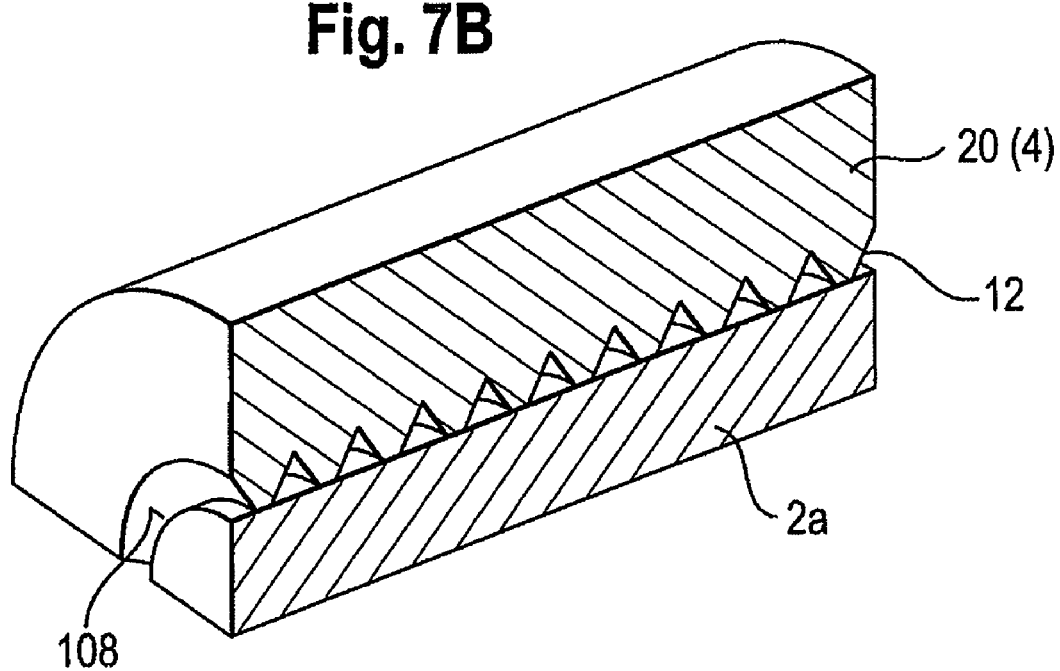
FIG. 7B shows a rod connection according to the first embodiment for carrying out a simulation.

FIG. 7A shows an input model for the simulation with a rod connection 101 according to prior art (no thread). FIG. 7B shows a corresponding model with the rod connection 1 of the bone stabilizing device (rod device 16) of FIG. 5B, i.e., with a metric thread 12. The rod receiving member 4 (first section 20) and the rod receiving member 104, respectively, have a wall thickness of 1.75 mm and an outer diameter of 5.5 mm. Its pipe length amounts to 6 mm. The rod receiving members 20(4), 104 are formed from a Titanium alloy. The rod-like member is a Nitinol-wire having a diameter of 2 mm with an interference of 0.020 mm. The friction coefficient µ amounts to 0.3.

Figure 8A:
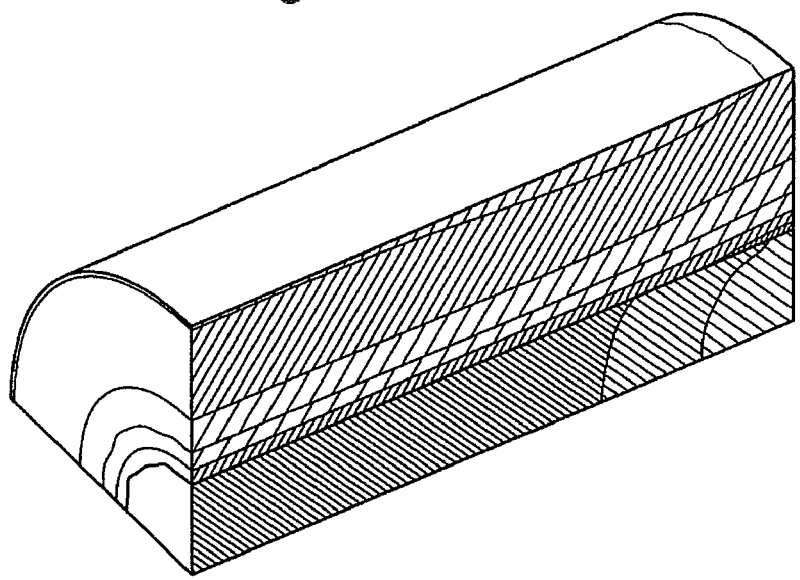
FIG. 8A shows the distribution of shear stress upon insertion of the rod part in the model shown in FIG. 7A.
Figure 8B:
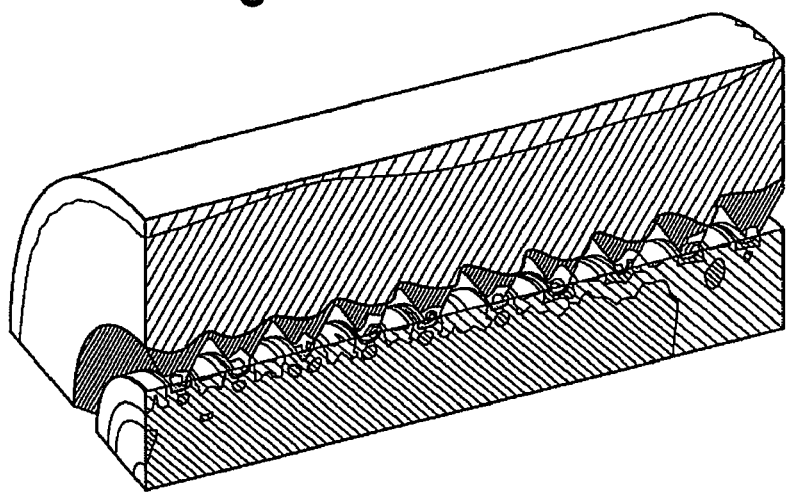
FIG. 8B shows the distribution of shear stress upon insertion of the rod part in the model shown in FIG. 7B.
Figure 12:
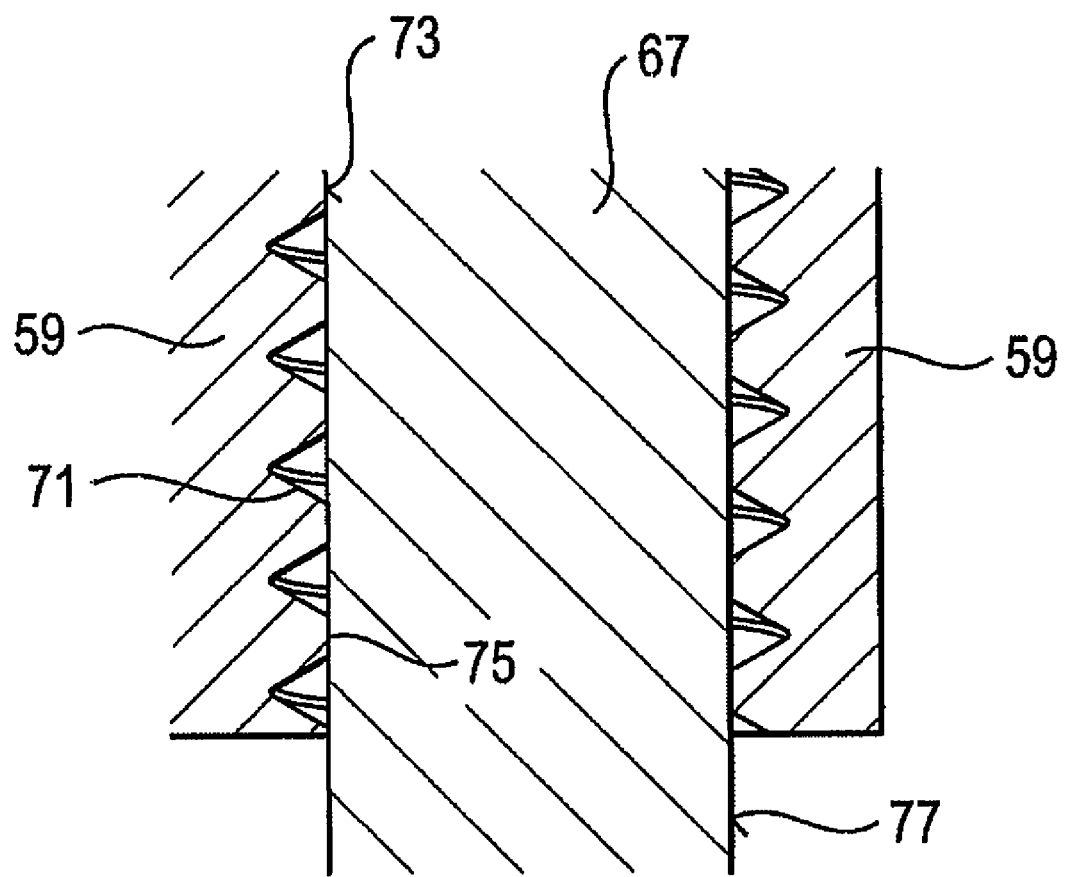
FIG. 12 shows a partially enlarged view of FIG. 10A with the rotational shaft being press-fitted within the bore of the pushing rod.

FIGS. 8A and 8B show respective results in terms of stress. Although the teeth-like helical projections of the thread indicate large local amounts of stress, the rod connection 1 with metric thread has an overall moderate distribution of stress in contrast to the case without a thread (i.e., FIG. 8A). The calculated insertion forces amounted to $F_1$=5.370 N for rod connection 101 according to prior art, and to $F_2$=2.120 N for rod connection 1 according to the first embodiment.

A second embodiment will be explained with reference to FIGS. 9-12. FIG. 9 shows an angular measurement device 51 for clinical surgery applications. A shifting element 57 may be manually pushed in longitudinal direction of the main body housing 53 with an actuator (not shown). Depending on the shift position of the shifting element 57 an opening angle of plate-like members 61, 63 is achieved. Thereby, the plate-like members pivot around a shaft axis 65 held on support arms 66.

The shift position of the shifting element 57 is converted into a pivoting movement of the plate-like members 61, 63 by virtue of a connecting member 59. The connecting member 59 has a shaft hole 69 through which a shaft (not shown in FIG. 9) mounted to the shifting element 57 extends such that the connecting member 59 is rotatable relative to the shaft.

Further, as shown in FIGS. 10, 11A and 11B, the connecting member 59 has a bore 73 through which a further shaft 67 extends. The shaft 67 is press-fitted with an amount of interference within the bore 73 to provide a rigid rod connection 1 with the connecting member 59. A metric thread 71 is provided at an inner wall surface 75 of the bore 73 (see partially enlarged view of FIG. 12). The shaft 67 has an even outer wall surface 77. It projects from the bore 73 on both sides thereof to engage with corresponding holes of the plate-like member 61. Thereby, the shaft 67 is rotatable with regard to the plate-like member 61.

It may be noted that the rod receiving member 4 according to the principle shown in FIG. 2 corresponds to the connecting element 59 of this embodiment, and the rod-like member 2 of FIG. 2 corresponds with respect to its function to shaft 67 of this embodiment.

It is further noted that the scope of the present invention also encompasses embodiments, in which the at least one recess is formed on the outer wall surface of the rod-like member. More specifically, the recesses on the outer wall surfaces may have similar shapes as detailed with respect to the embodiments as provided above, e.g., external thread patterns or regular patterns, etc.

What is claimed is:

1. A bone stabilization device comprising:
a rod having an end portion with an outer radius;
a rigid rod receiving member having a bore with an inner radius smaller than the outer radius, such that a press-fit connection is formed when the end portion of the rod is inserted into the bore of the rod receiving member; and
wherein one of an outer surface of the end portion of the rod and an inner surface of the bore of the rod receiving member has at least one recess while an entire length of the other one of the surfaces that is configured to be press-fit has a constant cross-section, wherein when the recess is on the inner surface of the bore, a radius of the bore at the recess is greater than the outer radius of the end portion of the rod, and when the recess is on the outer surface of the end portion of the rod, a radius of the end portion at the recess is smaller than the inner radius of the bore, to reduce a contact area at the press-fit connection when the end portion of the rod is inserted in the bore of the rod receiving member.

2. The bone stabilization device according to claim 1, wherein the rod and the rod receiving member each comprises a metal.

3. The bone stabilization device according to claim 2, wherein at least one of the rod and the rod receiving member comprise Titanium or a Titanium alloy.

4. The bone stabilization device according to claim 2, wherein the rod receiving member comprises Titanium or a Titanium alloy, and the rod comprises Nitinol.

5. The bone stabilization device according to claim 1, wherein the at least one recess is provided by a thread formed in the inner surface of the bore or the outer wall surface of the end portion of the rod.

6. The bone stabilization device according to claim 1, wherein the at least one recess is formed to reduce contact surface area between the rod receiving member and the rod by more than 20% and less than 80% as compared with a form fit connection therebetween.

7. The bone stabilization device according to claim 1, wherein the at least one recess forms a regular or homogeneously distributed pattern within the bore.

8. The bone stabilization device according to claim 1, wherein an inner diameter of the bore amounts to 4 mm or less.

9. The bone stabilization device according to claim 1, wherein an inner diameter of the bore amounts to 3 mm or less.

10. The bone stabilization device according to claim 1, wherein an inner diameter of the bore amounts to 2 mm or less.

11. The bone stabilization device according to claim 1, wherein the bore has a longitudinal axis, wherein a length of contact surface between the receiving member and the rod extending in the direction of the longitudinal axis amounts to more than 4 mm.

12. The bone stabilization device according to claim 11, wherein the length of the contact surface between the rod receiving member and the rod extending in the direction of the longitudinal axis amounts to more than 6 mm.

13. The bone stabilization device according to claim 1, further comprising a bone anchoring device comprising a bone anchoring element and a receiving part connected to the bone anchoring element, wherein the rigid rod receiving member is configured to connect to the receiving part.

14. A rod-shaped bone stabilization device for connecting two or more bone anchoring elements, the rod shaped bone stabilization device comprising:
   a first section and a second section each being connectable to one of said bone anchoring elements, the first section having a bore with an inner radius;
   a flexible section extending between the first section and the second section and providing elasticity in an axial direction;
   a rod having a first end portion with an outer radius greater than the inner radius of the bore and a second end portion, such that a press-fit connection is formed when the first end portion of the rod is inserted into the bore of the first section;
   wherein one of an outer surface of the first end portion of the rod and an inner surface of the bore of the first section has at least one recess while an entire length of the other one of the surfaces that is configured to be press-fit has a constant cross-section, wherein when the recess is on the inner surface of the bore, a radius of the bore at the recess is greater than the outer radius of the first end portion of the rod, and when the recess is on the outer surface of the first end portion of the rod, a radius of the first end portion at the recess is smaller than the inner radius of the bore, to reduce a contact area at the press-fit connection when the first end portion of the rod is inserted in the bore of the first section; and
   wherein the rod extends through the flexible section towards the second section, in which the second end portion of the rod is slidably supported such as to provide bending elasticity.

15. The rod shaped bone stabilization device according to claim 14, wherein the second section comprises a sliding support member for slidingly guiding the second end portion of the rod.

16. A method of attaching a bone stabilization device to a bone, the bone stabilization device comprising a rod having an end portion with an outer radius, a rigid rod receiving member having a bore with an inner radius smaller than the outer radius, such that a press-fit connection is formed when the end portion of the rod is inserted into the bore of the rod receiving member, and wherein one of an outer surface of the end portion of the rod and an inner surface of the bore of the rod receiving member has at least one recess while an entire length of the other one of the surfaces that is configured to be press-fit has a constant cross-section, wherein when the recess is on the inner surface of the bore, a radius of the bore at the recess is greater than the outer radius of the end portion of the rod, and when the recess is on the outer surface of the end portion of the rod, a radius of the end portion at the recess is smaller than the inner radius of the bore, to reduce a contact area at the press-fit connection when the end portion of the rod is inserted in the bore of the rod receiving member, the method comprising:
   aligning the end portion of the rod with the bore of the rod receiving member; and
   inserting the end portion of the rod into the bore of the rod receiving member to form the press fit connection.

17. The method according to claim 16, further comprising attaching a bone anchoring element to a bone, wherein the rod receiving member is connected to the bone anchoring element.

18. A bone stabilization device comprising:
   a rod having an end portion with an outer radius;
   a rigid rod receiving member having a bore with an inner radius smaller than the outer radius, such that a press-fit connection is formed when the end portion of the rod is inserted into the bore of the rod receiving member; and
   wherein at least one of an outer surface of the end portion of the rod and an inner surface of the bore of the rod receiving member has at least one recess, wherein when the recess is on the inner surface of the bore, a radius of the bore at the recess is greater than the outer radius of the end portion of the rod, and when the recess is on the outer surface of the end portion of the rod, a radius of the end portion at the recess is smaller than the inner radius of the bore, to reduce a contact surface area at the press-fit connection when the end portion of the rod is inserted in the bore of the rod receiving member; and
   wherein the at least one recess is formed to reduce the contact surface area between the rod receiving member and the rod by more than 20% and less than 80% as compared with a form fit connection therebetween.

19. A bone stabilization device comprising:
   a rod having an end portion with an outer radius;
   a rigid rod receiving member having a bore with an inner radius smaller than the outer radius, such that a press-fit connection is formed when the end portion of the rod is inserted into the bore of the rod receiving member; and
   wherein at least one of an outer surface of the end portion of the rod and an inner surface of the bore of the rod receiving member has at least one recess, wherein when the recess is on the inner surface of the bore, a radius of the bore at the recess is greater than the outer radius of the end portion of the rod, and when the recess is on the outer surface of the end portion of the rod, a radius of the end portion at the recess is smaller than the inner radius of the bore, to reduce a contact area at the press-fit connection when the end portion of the rod is inserted in the bore of the rod receiving member; and
   wherein the bore has a longitudinal axis, wherein a length of a contact surface between the receiving member and the rod extending in the direction of the longitudinal axis amounts to more than 4 mm.

20. The bone stabilization device according to claim 19, wherein the length of the contact surface between the rod receiving member and the rod extending in the direction of the longitudinal axis amounts to more than 6 mm.

* * * * *

UNITED STATES PATENT AND TRADEMARK OFFICE
CERTIFICATE OF CORRECTION

PATENT NO.         : 8,353,936 B2
APPLICATION NO.    : 12/242649
DATED              : January 15, 2013
INVENTOR(S)        : Lutz Biedermann et al.

It is certified that error appears in the above-identified patent and that said Letters Patent is hereby corrected as shown below:

In the Claims

| | |
|---|---|
| Column 7, Claim 6, line 2 | After "reduce" Insert -- a -- |
| Column 7, Claim 11, line 20 | After "of" Insert -- a -- |
| Column 7, Claim 14, line 36 | Delete "hone" Insert -- bone -- |

Signed and Sealed this
Twenty-fifth Day of February, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,353,936 B2 | Page 1 of 1 |
| APPLICATION NO. | : 12/242649 | |
| DATED | : January 15, 2013 | |
| INVENTOR(S) | : Biedermann et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 956 days.

Signed and Sealed this
Sixteenth Day of December, 2014

Michelle K. Lee
*Deputy Director of the United States Patent and Trademark Office*